(12) United States Patent
Carron

(10) Patent No.: US 9,737,375 B2
(45) Date of Patent: Aug. 22, 2017

(54) DENTAL HANDPIECE AND PROPHY ANGLE

(71) Applicant: AVID, Inc., Bloomsdale, MO (US)

(72) Inventor: Chris J. Carron, Bloomsdale, MO (US)

(73) Assignee: AVID, INC., Bloomsdale, MO (US)

( * ) Notice: Subject to any disclaimer, the term of this patent is extended or adjusted under 35 U.S.C. 154(b) by 83 days.

(21) Appl. No.: 14/736,518

(22) Filed: Jun. 11, 2015

(65) Prior Publication Data
US 2016/0361136 A1    Dec. 15, 2016

(51) Int. Cl.
*A61C 3/06*    (2006.01)
*A61C 1/14*    (2006.01)
*A61C 17/00*    (2006.01)

(52) U.S. Cl.
CPC ............ *A61C 1/141* (2013.01); *A61C 17/005* (2013.01)

(58) Field of Classification Search
CPC ......... A61C 1/18; A61C 1/185; A61C 17/005; A61C 1/141
See application file for complete search history.

(56) References Cited

U.S. PATENT DOCUMENTS

| | | |
|---|---|---|
| 3,163,934 A | 1/1965 | Wiseman |
| 3,509,629 A | 5/1970 | Mansano Kidokoro et al. |
| 3,740,853 A | 6/1973 | Brahler |
| 3,769,707 A | 11/1973 | Condon |
| 3,775,849 A | 12/1973 | Condon |
| 3,847,154 A | 11/1974 | Nordin |
| 3,939,599 A | 2/1976 | Henry et al. |
| 4,053,983 A | 10/1977 | Flatland |
| 4,278,429 A | 7/1981 | Straihammer et al. |
| 4,310,310 A | 1/1982 | Bailey |
| 4,827,552 A | 5/1989 | Bojar et al. |
| 5,007,832 A | 4/1991 | Meller et al. |
| 5,020,281 A | 6/1991 | Neff |
| 5,020,994 A | 6/1991 | Huang |
| 5,028,233 A | 7/1991 | Witherby |
| 5,040,978 A | 8/1991 | Falcon et al. |

(Continued)

FOREIGN PATENT DOCUMENTS

| | | |
|---|---|---|
| AU | 2010201843 A1 | 5/2010 |
| BR | PI0607986-5 A2 | 10/2009 |
| WO | WO2006/099469 | 9/2006 |

OTHER PUBLICATIONS

American National Standard Institute/American Dental Association (ANSI/ADA) Specification No. 85—Part 1 (Aug. 25, 2004).

*Primary Examiner* — Glenn Richman

(57) ABSTRACT

A combination includes a dental handpiece and a prophy angle. The dental handpiece includes a nosecone threadably connected to the dental handpiece. The prophy angle includes a proximal body that matingly attaches to the nosecone. A plurality of elongated torque members are formed on each of the prophy angle proximal body and the nosecone. Each of the torque members is a male torque member or a female torque member and each male torque member formed on one of the prophy angle proximal body and the nosecone matingly couples with a female torque member formed on the other of the nosecone and the prophy angle proximal body. The prophy angle, including the plurality of elongated torque members formed on the prophy angle, is formed to also be attachable to a known standard doriot-style nosecone. Other specific features of the handpiece and prophy angle are also disclosed.

23 Claims, 9 Drawing Sheets

(56) References Cited

U.S. PATENT DOCUMENTS

| | | |
|---|---|---|
| 5,062,796 A | 11/1991 | Rosenberg |
| 5,120,220 A | 6/1992 | Butler |
| 5,156,547 A | 10/1992 | Bailey |
| 5,178,538 A | 1/1993 | Eckert |
| 5,209,658 A | 5/1993 | Brahler |
| 5,328,369 A | 7/1994 | Bailey |
| 5,340,310 A | 8/1994 | Bifulk |
| 5,348,473 A | 9/1994 | Kivlighan, Jr. |
| 5,352,119 A | 10/1994 | Sakurai |
| 5,380,202 A | 1/1995 | Brahler |
| 5,433,605 A | 7/1995 | Strobl, Jr. |
| 5,482,461 A | 1/1996 | Yale |
| 5,484,284 A | 1/1996 | Bailey |
| 5,496,218 A | 3/1996 | Brahler |
| 5,529,495 A | 6/1996 | Edwards |
| 5,531,599 A | 7/1996 | Bailey |
| 5,549,634 A | 8/1996 | Scott et al. |
| 5,571,012 A | 11/1996 | Witherby et al. |
| 5,575,799 A | 11/1996 | Bolanos et al. |
| 5,642,995 A | 7/1997 | Bailey |
| 5,645,426 A | 7/1997 | Grim et al. |
| 5,674,068 A | 10/1997 | Eibofner |
| 5,683,247 A | 11/1997 | Bailey |
| 5,692,901 A | 12/1997 | Roth et al. |
| 5,730,595 A | 3/1998 | Bailey |
| 5,797,744 A | 8/1998 | Rosenberg |
| 5,871,353 A | 2/1999 | Pierce et al. |
| 5,902,107 A | 5/1999 | Lowell |
| 5,911,577 A | 6/1999 | Henrikson |
| 5,924,864 A | 7/1999 | Logé et al. |
| 5,931,672 A | 8/1999 | Postal et al. |
| 5,941,705 A | 8/1999 | Makris et al. |
| 5,964,590 A | 10/1999 | Loddeke et al. |
| 5,980,248 A | 11/1999 | Kusakabe et al. |
| 6,012,922 A | 1/2000 | Novak |
| 6,042,377 A | 3/2000 | Ito |
| 6,050,989 A | 4/2000 | Fox et al. |
| 6,053,732 A | 4/2000 | Sale |
| 6,083,000 A | 7/2000 | Charlton |
| 6,089,866 A | 7/2000 | Brahler |
| 6,099,309 A | 8/2000 | Cardarelli |
| 6,128,397 A | 10/2000 | Baluja et al. |
| 6,168,433 B1 | 1/2001 | Hamlin |
| 6,203,322 B1 | 3/2001 | Kraenzle |
| 6,257,886 B1 | 7/2001 | Warner |
| 6,270,345 B1 | 8/2001 | Abbott et al. |
| 6,315,559 B1 | 11/2001 | Nakanishi |
| 6,382,971 B1 | 5/2002 | Randolph |
| 6,579,093 B2 | 6/2003 | Bailey et al. |
| 6,655,015 B2 | 12/2003 | Kraenzle |
| 7,153,133 B1 | 12/2006 | Chia et al. |
| 7,160,108 B2 | 1/2007 | Jaffe |
| 7,255,559 B2 | 8/2007 | Shen et al. |
| 7,338,285 B1 | 3/2008 | Balaban |
| 7,422,433 B2 | 9/2008 | Carron et al. |
| 7,762,813 B2 | 7/2010 | Seals et al. |
| 7,955,079 B2 | 6/2011 | Chronister et al. |
| 8,123,523 B2 | 2/2012 | Carron et al. |
| 8,360,774 B2 | 1/2013 | Carron et al. |
| 8,459,992 B2 | 6/2013 | Carron et al. |
| 8,597,022 B2 | 12/2013 | Carron et al. |
| 8,668,494 B2 | 3/2014 | Carron et al. |
| 8,764,442 B2 | 7/2014 | Mansour |
| 8,777,615 B2 | 7/2014 | Hayman et al. |
| 8,784,102 B1 | 7/2014 | Kumar |
| 8,814,566 B2 | 8/2014 | Carron et al. |
| 8,834,159 B2 | 9/2014 | Carron et al. |
| D716,946 S | 11/2014 | Wilson |
| 2008/0311541 A1 | 12/2008 | Carron et al. |
| 2009/0081609 A1 | 3/2009 | Kalbfeld et al. |
| 2009/0220910 A1 | 9/2009 | Wang |
| 2010/0015568 A1 | 1/2010 | Carron et al. |
| 2010/0035205 A1 | 2/2010 | Wang et al. |
| 2011/0065063 A1 | 3/2011 | Bock |
| 2011/0244420 A1 | 10/2011 | Chronister et al. |
| 2012/0156643 A1 | 6/2012 | Carron et al. |
| 2012/0214126 A1 | 8/2012 | Carron et al. |
| 2013/0130198 A1 | 5/2013 | Carron et al. |
| 2014/0141386 A1 | 5/2014 | Madry et al. |

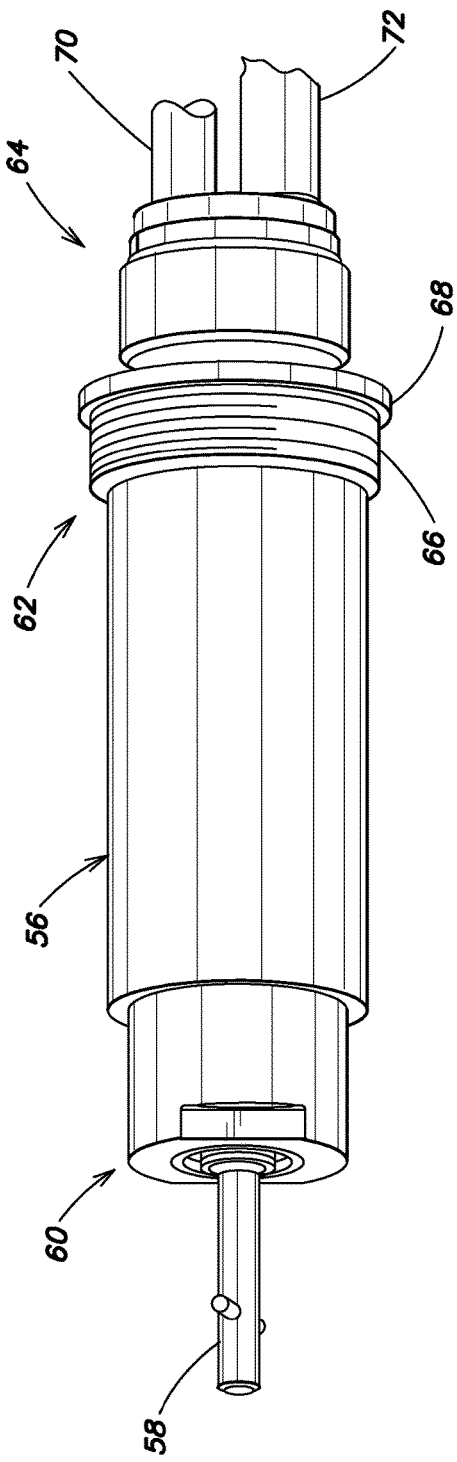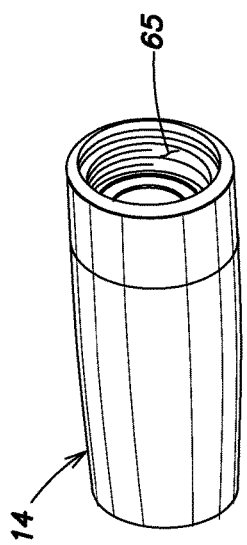
FIG. 4
FIG. 5

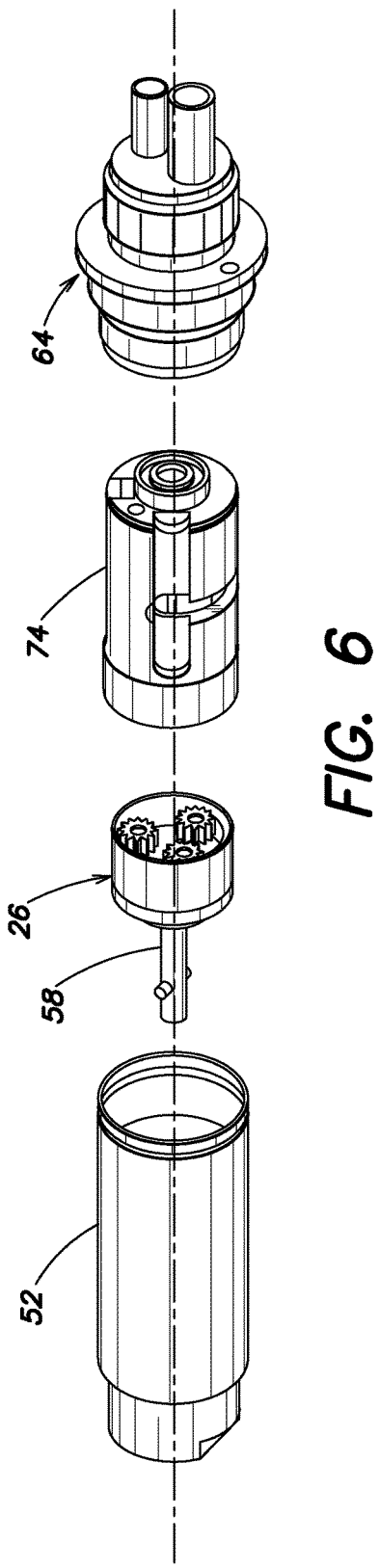

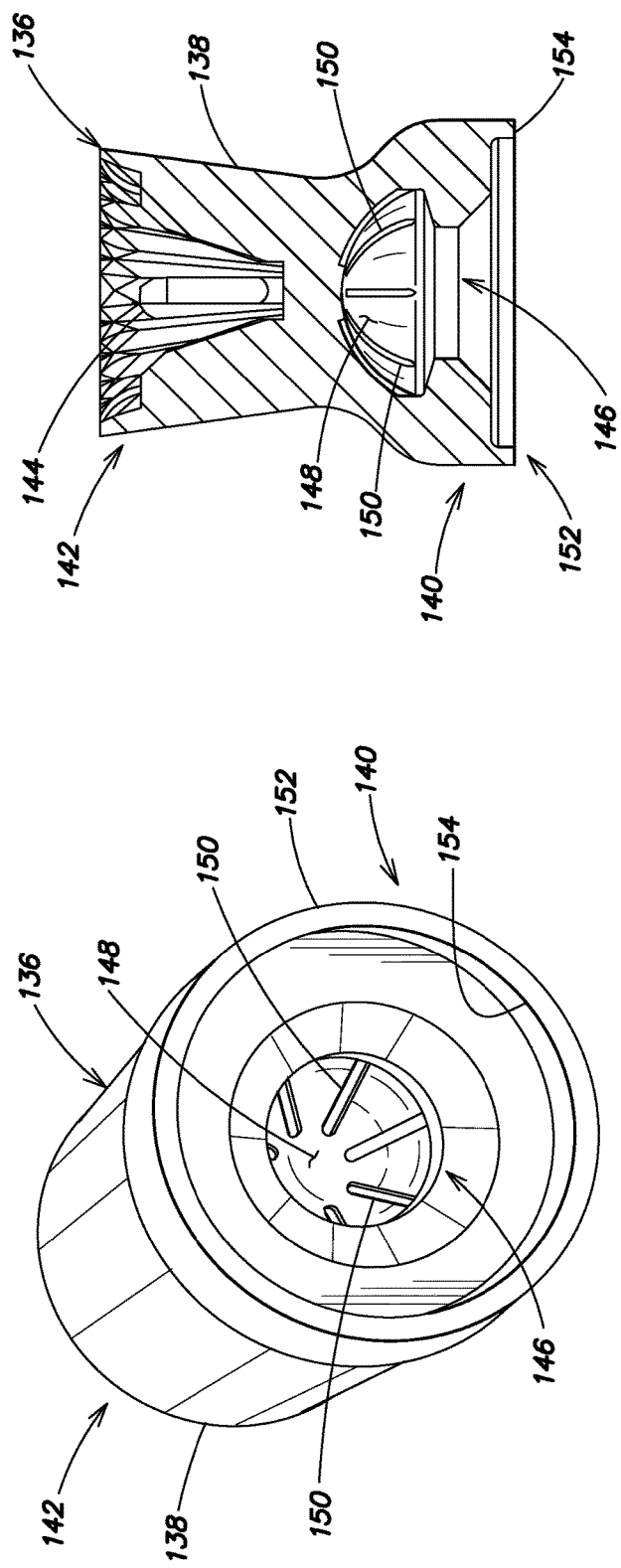
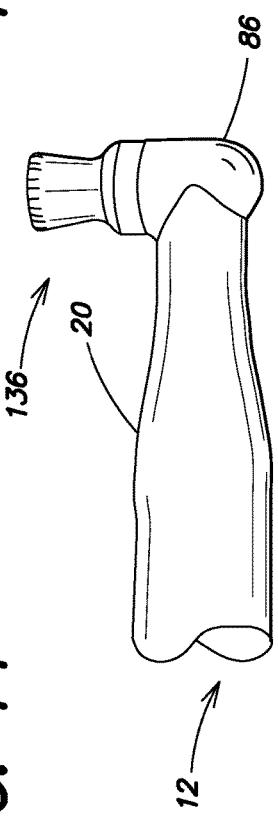
FIG. 14
FIG. 15
FIG. 16

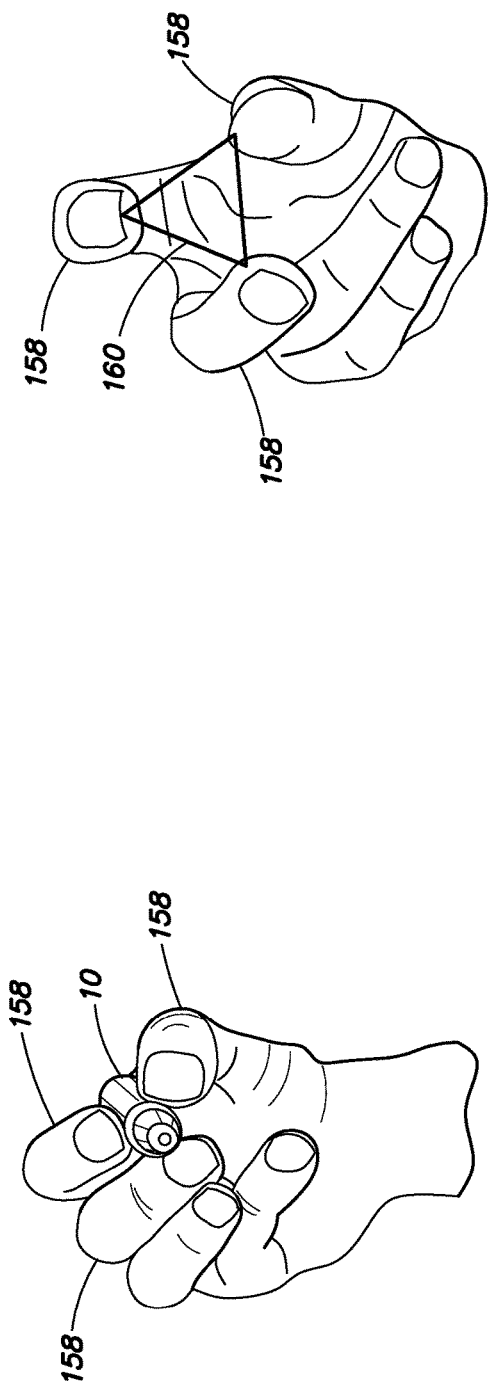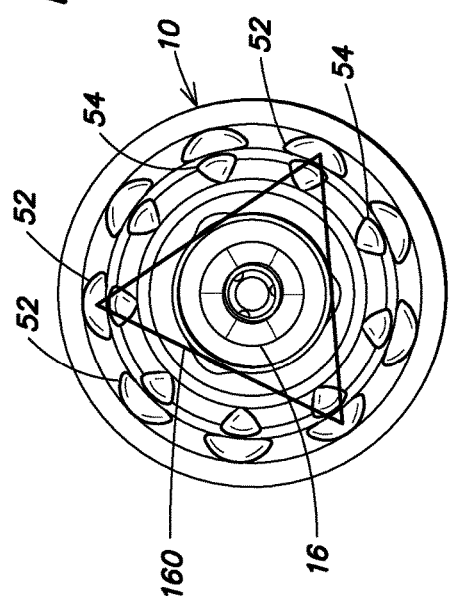

DENTAL HANDPIECE AND PROPHY ANGLE

FIELD

The present disclosure relates to a prophy angle and a dental handpiece for connection to and for powering the prophy angle.

BACKGROUND

This section provides background information related to the present disclosure which is not necessarily prior art.

Dental prophylaxis angles, generally referred to as "prophy angles", are commonly used dental instruments providing rotation for dental tools such as brushes, prophy cups, or other receptacles used in polishing teeth. A prophy angle typically includes a housing having a neck and a head portion extending at approximately a 90° angle to the neck, which increases the ability of a dentist to access the varying teeth surfaces of a patient. A drive shaft may be located within the housing and attached to a driven gear in the head of the prophy angle.

Prophy angles are generally affixed to a handpiece, for powering and driving the prophy angle drive shaft. The handpiece may be powered by any number of sources, such as pneumatic, electrical, or batteries. Prophy angles are commonly manufactured from lightweight plastic to make them inexpensive enough to be disposable, thereby increasing overall sterility in the dental environment. An issue associated with making the prophy angles, and their constituent elements, such as the driven gear and drive shaft, from plastic is the ability of the handpiece to engage the drive shaft and the driven gear without excessive damage to the prophy angle.

A reduction in the number of component parts needed for constructing and assembling a prophy angle is desirable. In addition, designing the component parts to cooperatively operate with other component parts reliably and in an efficient manner is also desirable.

A standard well known doriot-style prophy angle includes a generally cylindrical or frustoconical inner wall that mates with a similarly-shaped nosecone of a handpiece. In addition, the doriot-style prophy angle typically includes a notched section that fits with a mating protrusion on the handpiece to key or orient the prophy angle with respect to the handpiece. For a handpiece having an angle-adjustable nosecone, the notched section and frictional forces may provide an unsatisfactory fixation force, between the prophy angle and the nosecone, not allowing the desired angle of the nosecone to be reliably locked and unlocked, during a procedure, because the prophy angle may slip/rotate with respect to the nosecone. Therefore, for a handpiece nosecone having an adjustable angle, providing an easy, quick, and reliable way of adjusting the angle and setting or locking the desired angle is desirable.

SUMMARY

This section provides a general summary of the disclosure, and is not a comprehensive disclosure of its full scope or all of its features.

One example disclosed is a combination of a dental handpiece and a prophy angle. The dental handpiece may include a body and a nosecone threadably connected to a distal portion of the dental handpiece. The prophy angle may include a proximal body such that the prophy angle proximal body is matingly attached to the nosecone. A plurality of elongated torque members may be formed on each of the prophy angle proximal body and the nosecone, wherein each of the plurality of elongated torque members is one of a male torque member and a female torque member, such that each male torque member formed on one of the prophy angle proximal body and the nosecone matingly couples with a female torque member formed on the other of the nosecone and the prophy angle proximal body. The prophy angle, including the plurality of elongated torque members formed on the prophy angle, is formed to also be attachable to a known standard doriot-style nosecone.

Another example disclosed is a prophy angle having a proximal body for attachment to a dental handpiece nosecone and a head formed on a distal end of the proximal body. A gear assembly may be a combination of a face-gear and a spur-gear. A drive shaft may be rotatably held within the proximal body, including one of the face-gear and the spur-gear formed on a distal end of the drive shaft. A rotor assembly includes a portion rotatably held within the head and the other of the face-gear and the spur-gear may be formed on the rotor assembly such that the rotor assembly is driven by the drive shaft via the gear assembly. A bearing member may form a portion of the rotor assembly and may be rotatably held within the head. The bearing member is symmetrical about a rotation axis of the rotor assembly. A mating bearing member may be attached distally with respect to the drive shaft distal end such that the bearing member matingly couples with the mating bearing member as the drive shaft and the rotor assembly are rotated. The bearing member contacts less than half of the mating bearing member during rotation and structure may form a void radially inward with respect to a plurality of teeth forming the face-gear.

A further example disclosed is a dental handpiece for rotatably driving a dental tool including a body and a nosecone connected to a distal portion of the dental handpiece, wherein the nosecone is for coupling with a prophy angle. An engine cartridge may be held within the body and is sized and adapted for containing one of a plurality of engine types. The engine cartridge further may include a drive member extending from an engine cartridge distal end, the drive member being rotatably driven by one of the plurality of engine types and the engine cartridge including a proximal end for connection to one of a plurality of types of power source connectors. A proximal end of the body includes structure for connection to each of the plurality of types of power source connectors.

Another example disclosed is a dental prophy cup having a body with a proximal portion and a distal portion. A cup may be formed on the body distal portion. A rotor cavity may be formed within the body proximal portion. A rotor contact surface may form a portion of the rotor cavity and have a profile for matingly coupling with a rotor surface.

Still another example disclosed is a dental prophy angle having proximal body for attachment to a dental handpiece nosecone. A drive shaft may be rotatably held within the proximal body and extend beyond a proximal end of the prophy angle. A retainer may be held within the proximal body and surround a portion of the drive shaft, a distal end of the retainer may form a bearing surface for a gear attached to a distal end of the drive shaft. A retention boss may be formed on and surround the retainer. A cross-section of the retention boss may taper to an outer edge. A retention groove may be formed in the proximal body for mating attachment with the retention boss such that a portion of the retention boss is compressed within the retention groove.

Yet another example disclosed is a dental prophy angle having a proximal body for attachment to a dental handpiece nosecone and a head formed on a distal end of the proximal body. A rotor assembly may include a portion rotatably held within the head and a retention flange extending radially from the rotor assembly. A retention boss may extend from an interior surface of the head and be located above the rotor assembly retention flange. The retention boss forms an arc of less than three hundred sixty degrees.

A yet further example disclosed is a dental handpiece having a body; and a nosecone assembly attached to a distal end of the body. The nosecone assembly may include a proximal base section for attachment to the handpiece body distal end. A ball nose may be pivotally engaged with the proximal base section. A ball lock may surround a portion of the proximal base section and a portion of the ball nose. A flexible ring seal may surround a portion of the ball nose and may be positioned between the ball nose and an interior surface of the ball lock. A nosecone may be threadably coupled with the ball nose. A locking seal may surround a distal portion of the ball lock and a proximal portion of the nosecone. As the nosecone is increasingly threaded onto the ball nose, a frictional contact force is increased between the ball lock and each of the proximal base section, the ball nose, and the locking seal.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a perspective of a portion of the handpiece of FIG. 1;

FIG. 5 is a perspective of a body portion of the handpiece of FIG. 1;

FIG. 6 is an exploded perspective of FIG. 4;

FIG. 7 is another example of a portion of FIG. 6;

FIG. 8 is yet another example of a portion of FIG. 6;

FIG. 14 is a perspective of an example prophy cup;

FIG. 15 is a partial cut-away elevation of the example prophy cup;

FIG. 16 is a partial perspective of an example prophy angle with an attached prophy cup;

FIGS. 17A and 17B illustrate example hand grips of a user for an example handpiece; and FIG. 17C is a distal end elevation showing example finger recesses of an example handpiece.

Corresponding reference numerals indicate corresponding parts throughout the several views of the drawings.

DETAILED DESCRIPTION

Example embodiments will now be described more fully with reference to the accompanying drawings.

Figure 1:
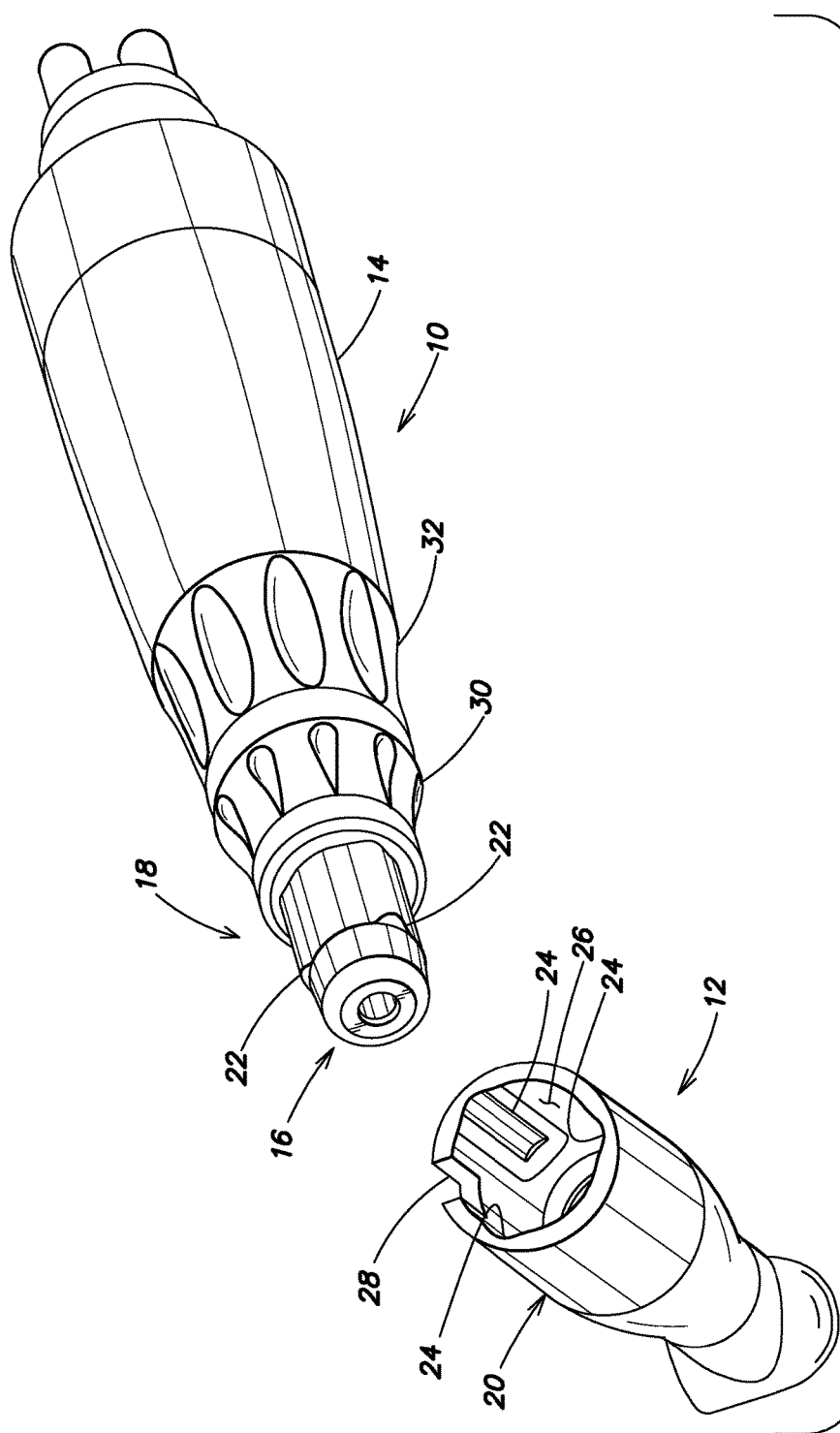
FIG. 1 is a modified exploded perspective of an example dental handpiece and a prophy angle.

An example combination of a dental handpiece 10 and a prophy angle 12 are shown in FIG. 1. The dental handpiece 10 may include a body 14 and a nosecone 16 threadably connected to a distal portion 18 of the dental handpiece 10. The prophy angle 12 may include a proximal body 20 such that the prophy angle proximal body 12 may be matingly attached to the nosecone 16. The operation of the example nosecone 16 and similar nosecones are known and therefore not described in detail. Generally, in the example disclosed, the nosecone 16 may be pivoted with respect to the handpiece 10 and locked at the desired angle by increasingly threading the nosecone onto the handpiece 10 until the nosecone is locked in place. More detailed explanations of similar nosecones, particularly details of the pivot structure, are provided in at least U.S. Pat. No. 8,834,159.

A plurality of elongated torque members may be formed on each of the prophy angle proximal body 20 and the nosecone 16. Each of the plurality of elongated torque members may be one of a male torque member and a female torque member, such that each male torque member formed on one of the prophy angle proximal body 20 and the nosecone 16 matingly couples with a female torque member formed on the other of the nosecone 16 and the prophy angle proximal body 20. In the example of FIG. 1, the nosecone 16 has a plurality of male torque members 22 (one torque member 22 is not seen in the FIG. 1 view) and the proximal body 20 may have a corresponding number of female torque members 24. In other examples the male torque members may be formed on the proximal body 20 with corresponding female torque members formed on the nosecone 16. As explained in more detail below, when in use, the mated torque members 22 and 24 provide a user grasping the proximal body with significant leverage to tighten and loosen the nosecone with respect to the handpiece 10 to select and set a desired angle of the nosecone with respect to the handpiece 10. Without the torque members, attempting to tighten or loosen the nosecone 16, during a procedure, may easily result in the prophy angle slipping and rotating about the nosecone; consequently, attaining the proper amount of leverage to loosen or tighten the nosecone may not be possible.

In addition, the prophy angle 12, including the plurality of elongated torque members 24 formed on the prophy angle 12, may be formed to also be attachable to a known standard doriot-style nosecone. This is accomplished, in the example of FIG. 1, by forming the inner wall 26 to have a diameter that mates with a standard doriot-style nosecone. Said another way, a portion of the proximal body forming inner wall 26, not including structure forming the three female torque members 24, frictionally attaches to the known standard doriot-style nosecone (not shown). For example, a standard doriot-style nosecone and a standard doriot-style prophy angle have dimensions as described in the American National Standard Institute/American Dental Association (ANSI/ADA) Specification No. 85-Part 1 (Aug. 25, 2004). All references, in the disclosed examples, to standard doriot-style nosecones and prophy angles and their respective parts should comply with this ANSI/ADA specification. Therefore, the inner wall 26 should have a diameter slightly larger to allow the prophy angle to be pushed on and pulled off of the standard doriot-style nosecone; yet, sized so that the proximal body is matingly coupled to the nosecone via a frictional interference. Additionally, the notch shown at 28 allows the prophy angle 12 to fit around mating structure of a standard doriot-style handpiece. It is also noted that, for clarity, the prophy angle 12 of FIG. 1 does not show any of the drive shaft, a rotary assembly, or a prophy cup.

In the example shown, the nosecone 16 includes three male torque members 22 and the prophy angle 12 includes three female torque members 24, though other configurations and numbers of torque members 22, 24 may be used, depending on the design and specification requirements. Further, the nosecone 16, including the plurality of elongated torque members 22 formed on nosecone, may be formed to prevent attachment to a known standard doriot-style prophy angle. That is to say a circumference defined by a top surface of each of the three male torque members 22 is sufficiently large to prevent the attachment of the nosecone 16 to the known standard doriot-style prophy angle. In this way only prophy angles 12 with mating torque members may be attached to nosecone 16 to ensure that a sufficient amount of force may be transferred to the nosecone 16 to ensure that the nosecone is locked relative to the body 14 during use.

It is noted that in another example (not shown) the mating torque members may be switched; such that the male torque members may be formed on the prophy angle proximal body and the female torque members may be formed on the nosecone or a combination of male and female torque members may be formed on each of the prophy angle proximal body and the nosecone. Said another way, a plurality of elongated torque members may be formed on the nosecone, wherein each of the plurality of elongated torque members is one of a male torque member and a female torque member, such that each male torque member formed on the nosecone is for matingly coupling with a female torque member formed on a mating prophy angle proximal body. In this example, similar to the FIG. 1 example, a circumference of an outermost top surface of the nosecone may be sufficiently large to prevent the attachment of the nosecone to the known standard doriot-style prophy angle.

Figure 2:
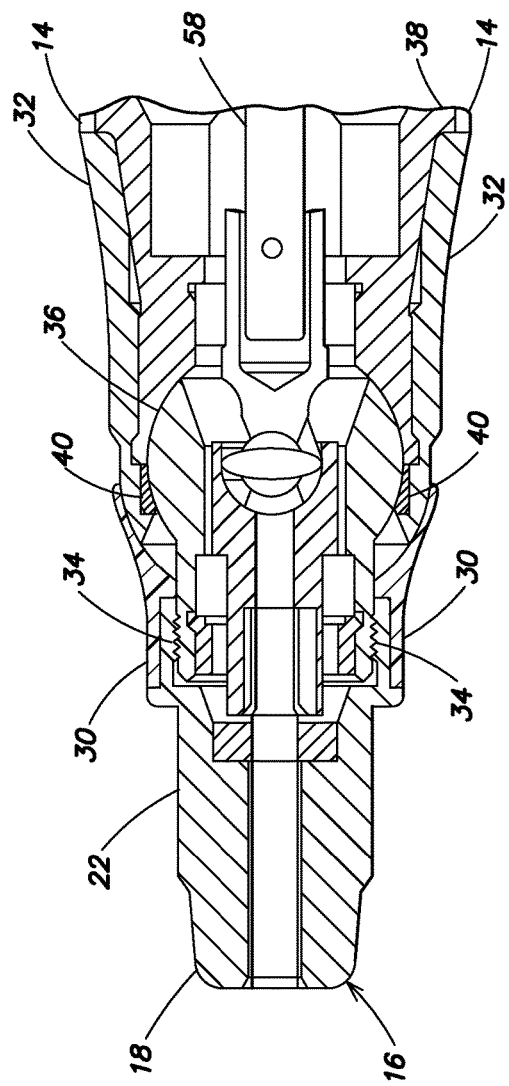
FIG. 2 is a partial cross section of the handpiece of FIG. 1.

The distal portion 18 may include a locking seal 30 and a ball lock 32 and related components contained within the locking seal 30 and the ball lock 32, as shown in FIG. 2. Of course, distal portion 18 may include other structure; for example, if the handpiece 10 does not have the capability of adjusting the angle of the nosecone 16 relative to the body 14, then much of the structure shown in FIG. 2 is not necessary, as those skilled in the art will appreciate. The example of FIG. 2 shows nosecone 16 threadably connected to distal portion 18 at 34. In this example, the distal portion 18 includes a ball nose 36 for the threaded attachment of nosecone 16.

The example of FIG. 2 may be described as a nosecone assembly attached to the body 14, where the nosecone assembly includes a proximal base section 38 for attachment to the handpiece body 14, the ball nose 36 pivotally engaged with the proximal base section 38, the ball lock 32 surrounding a portion of the proximal base section 38 and a portion of the ball nose 36, a flexible ring seal 40 surrounding a portion of the ball nose 36, wherein the flexible ring seal 40 is positioned between the ball nose 36 and an interior surface of the ball lock 32, the nosecone 16 threadably coupled with the ball nose 36, the locking seal 30 for surrounding a distal portion of the ball lock 32 and a proximal portion of the nosecone 16. In this example, as the nosecone 16 is increasingly threaded onto the ball nose 36, a frictional contact force is increased between the ball lock 32 and each of the proximal base section 38, the ball nose 36, and the locking seal 30. This allows a desired angle of the nosecone 16 to be set relative to the body 14 of handpiece 10 in a quick, efficient manner.

FIG. 2 shows further structure, not referenced, that is used to drive a prophy angle 12 attached to the nosecone 16.

Figure 3:
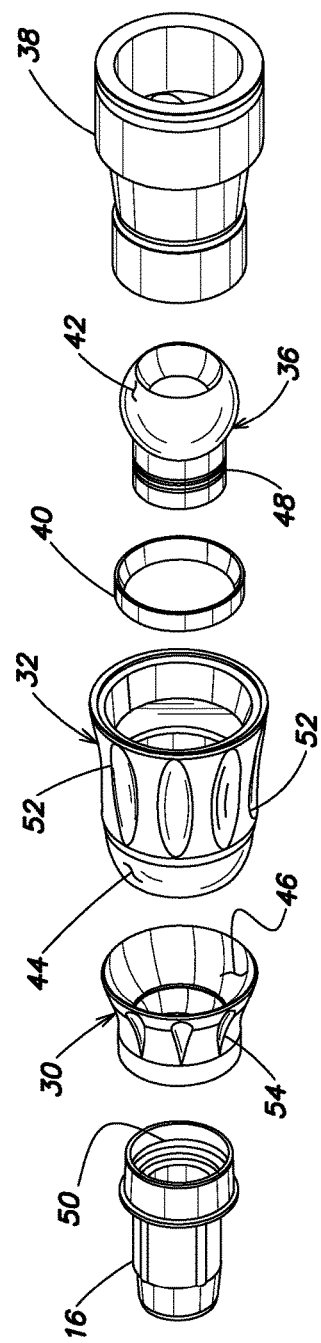
FIG. 3 is an exploded perspective of a portion of the handpiece of FIG. 1.

FIG. 3 is an exploded view of a portion of the components of FIG. 2. The proximal base section 38 may be formed of aluminum to provide light weight, durable construction. The ball nose 36 may be formed of aluminum, including at least a partially anodized exterior surface 42. By anodizing the exterior surface 42 (generally the spherical portion of ball nose 36) a useful life of ball nose 36 may be extended by increasing the resistance to wear compared to a non-anodized part. The ball lock 32 may be formed of aluminum, including at least a partially anodized exterior surface 44. Anodizing ball lock 32, at least at surface 44 may increase the useful life of ball lock 32 by increasing the wear resistance of surface 44 compared to a non-anodized surface. The nosecone 16 may be formed of aluminum, including at least a partially anodized exterior surface such as the surface that frictionally contacts a mating prophy angle (not shown in FIG. 3). Again, anodizing the exterior surface of nosecone 16 may extend the useful life of nosecone 16. The locking seal 30 may be formed of a suitable plastic and may have a portion of an interior surface 46 roughened. The roughened interior surface 46 is in frictional contact with anodized surface 44 of ball lock 32 and the roughened interior surface 46 may increase the effective locking force when a user applies torque to the nosecone 16 to lock-in a desired angle. In this manner, at least a frictional contact surface of each of the ball nose 36, the ball lock 32, and the locking seal 30 may be roughened for enhancing the frictional contact force. In the example of FIG. 3, the roughened frictional contact surfaces may include 42, 44, and 46. The interior surface (not shown in FIG. 3) of base portion 38 that contacts surface 42, may also be roughened.

FIG. 3 also shows threads 48 on ball nose 36 and threads 50 on nosecone 16 that together form the threaded connection 34 shown in FIG. 2.

FIG. 3 further shows that a plurality of finger recesses 52 and 54 equally spaced and formed around a periphery of each of the ball lock 32 and the locking seal 30. Interestingly, during development of handpiece 10, it was discovered that handpieces where a number of finger recesses 52, 54 are an integer multiple of three provides a user with a comfortable, stable grip as explained in detail below. The example shown includes nine finger recesses 52 and 54, though other integer multiples of three may also be acceptable, such as 3, 6, 12, or the like.

In addition to the dental handpiece 10 including body 14 and the nosecone 16 connected to a distal portion 18, the dental handpiece 10 may also include an engine cartridge held within the body 14. The engine cartridge may be sized and adapted for containing one of a plurality of engine types. An example engine cartridge 56 is shown in FIG. 4. The engine cartridge 56 may further include a drive member 58 extending from an engine cartridge distal end 60. The drive member 58 may be rotatably driven by one of the plurality of engine types, as explained further below. The engine cartridge 56 also includes a proximal end 62 for connection to one of a plurality of types of power source connectors 64 (and 78, 82 described below). A proximal end of the body 14 includes structure, such as threads 65 shown in FIG. 5, for connection to each of the plurality of types of power source connectors 64. In the example shown in FIG. 4, the base portion of power source connector 64 may be formed with threads 66 to mate to threads 65 formed in body 14. However, in other examples different structure for connection between the power source connectors 64 and body 14 may be used. For example, the boss or raised edge 68 may form a part of a snap-fit with body 14.

Each of the power source connectors 64 may include appropriate connections between the particular engine type and the power source for that engine type. The example, shown in FIG. 4, includes a pneumatically-driven motor and the connections to the power source (not shown) include an air supply line 70 for supplying pressurized air to drive the motor and an exhaust line 72 for routing exhausted air to a muffler (not shown) or other remote location. FIG. 6 shows the engine cartridge of FIG. 4 in exploded form. FIG. 6 shows an example engine 74 that rotatably drives drive member 58 via a drive assembly 76. The example drive assembly 76 includes a planetary gear assembly that is driven by a mating gear (not shown) on the engine 74. Of course, other appropriate drive arrangements may be utilized. The plurality of engine types may include an AC electrical motor, a battery-powered electrical motor, a pneumatically-driven motor, or any other appropriate type of engine to drive a prophy angle. Each engine type requires a corresponding power source connector. In the example of FIGS. 4 and 5, power source connector 64 is for a pneumatically-driven motor 74. For an AC electrical motor, a corresponding power source connector 78 is shown in FIG. 7 and includes an electrical cable 80 for connection to an electrical power source (not shown) such as a wall outlet. For a battery-powered electrical motor, a corresponding power source connector 82 is shown in FIG. 8 and includes a cap 84 that may be removed to insert batteries within connector 82. Example engines 74 may include any appropriate engine including motors specially designed for the example dental handpiece or commercially available engines from a variety of manufacturers. The use of off-the-shelf commercially produced engines is likely to be the most cost-effective, as these engines are typically produce in large quantities, thus reducing individual engine cost. It is also noted that each engine may include associated engine controller circuitry (not shown) for controlling the speed and other characteristics depending on the type of engine used.

The modular construction of the engine cartridge 56 and its associated component parts allows a manufacturer to reuse many components and reuse component parts even while providing customers with a range of power sources for handpiece 10. For example, through careful design and component selection it may be possible to make and sell a pneumatic, AC electrical, and a battery powered handpiece where all three different power options use the same body 14, engine cartridge 56, and drive assembly 76. Only the power source connectors need be different for each corresponding engine type. Compared to designs where each type of power source is individually designed, the disclosed modular engine cartridge designs allows for a significant reduction in the number of components needed to be held in inventory and because of the significant reuse of components across power source options the reuse components may be built and purchase in significantly greater volumes further reducing the per piece component cost.

Figure 9:
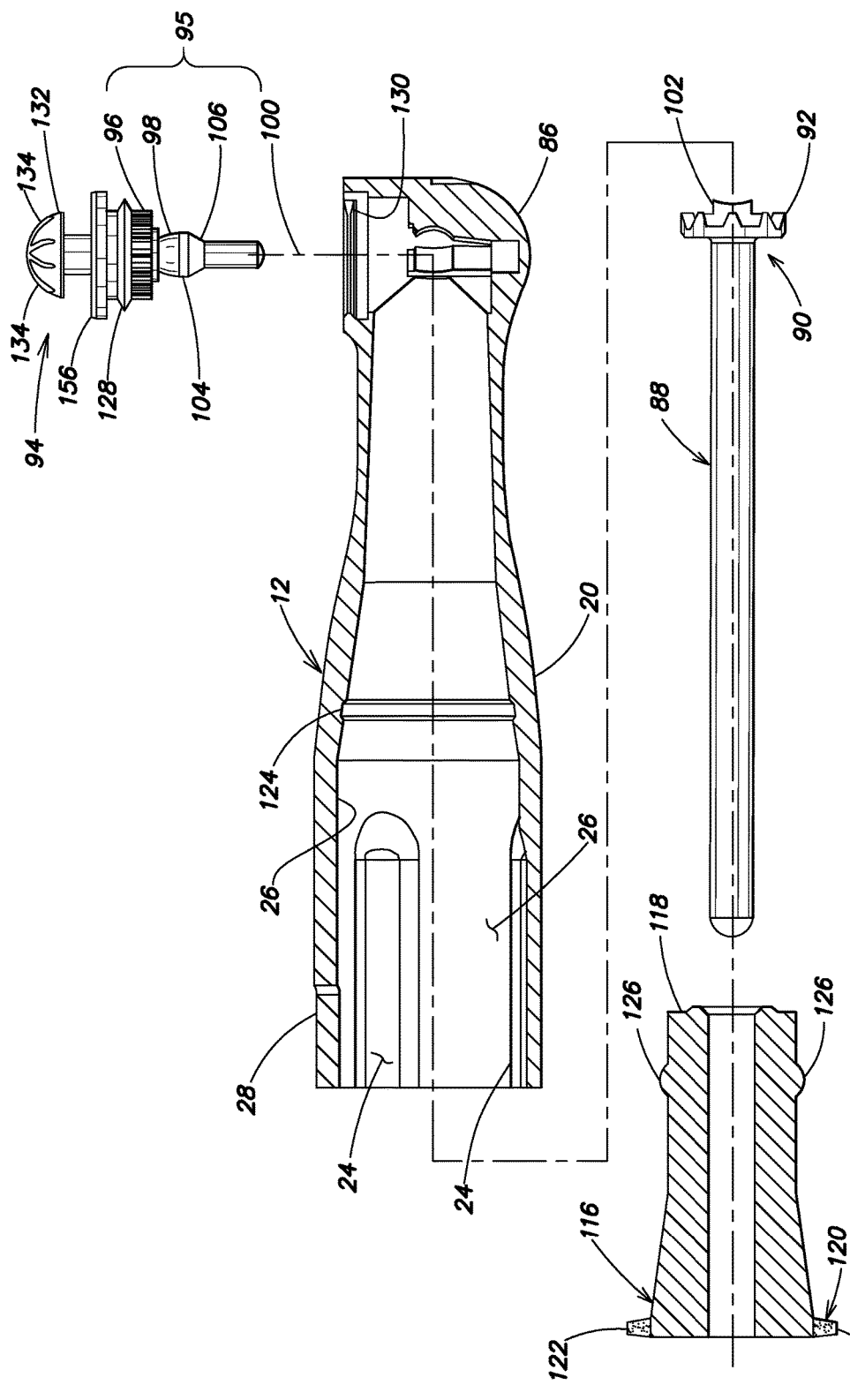
FIG. 9 is a modified exploded view of the example prophy angle of FIG. 1.

The prophy angle 12 of FIG. 1 is shown in cross section in FIG. 9 in a modified exploded view of an example prophy angle 12. Prophy angle 12 includes the proximal body 20. A plurality of elongated torque members 24 may be formed on the prophy angle proximal body 20. Each of the plurality of torque members 24 may be one of a male torque member and a female torque member, such that each male torque member formed on the prophy angle proximal body is for matingly coupling with a female torque member formed on a mating dental handpiece nosecone. In the example shown in FIG. 9, each of the three torque members 24 is a female torque member and mates with a corresponding male torque member on nosecone 16; however, each female torque member does not necessarily need to mate with a male torque member. As stated above, the prophy angle 12, including the plurality of elongated torque members 24 formed on the prophy angle, is formed to also be attachable to a known standard doriot-style dental handpiece nosecone. This is accomplished in the example shown, by having the diameter of inner wall 26 mate with the known standard doriot-style dental handpiece nosecone via a frictional interference.

The prophy angle 12 may also include a head 86 formed on a distal end of the proximal body 20 as shown. The prophy angle 12 may further include a gear assembly comprising a combination of a face-gear and a spur-gear, comprised of component parts described below.

A drive shaft 88 may be rotatably held within the proximal body 20 and may include one of the face-gear and the spur-gear formed on a distal end 90 of the drive shaft 88. In the example shown, distal end 90 has a face-gear 92 attached. A rotor assembly 94 may include a portion, shown generally at 95, rotatably held within the head 86. The rotor assembly 94 may further include the other of the face-gear and the spur-gear formed on the rotor assembly such that the rotor assembly 94 is driven by the drive shaft via the gear assembly. In the example shown, rotor assembly 94 includes the spur-gear 96.

Figure 10:
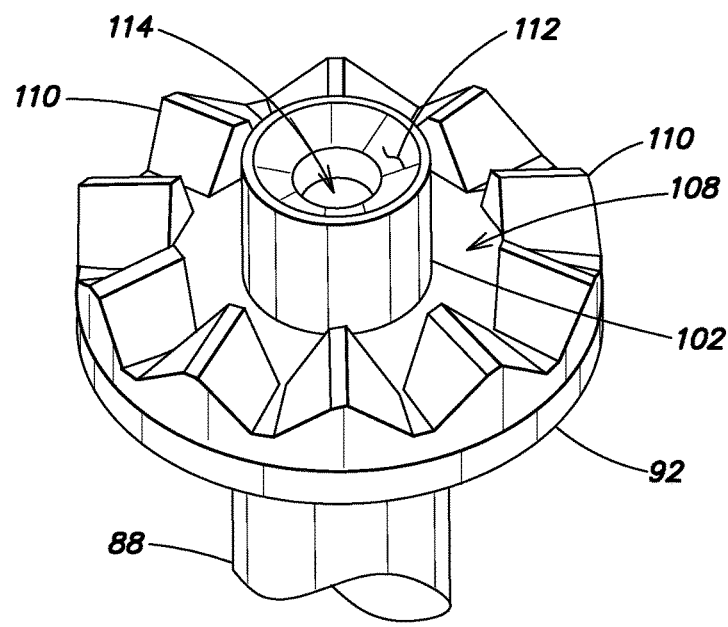
FIG. 10 is a partial perspective of a portion of FIG. 9.

A bearing member 98 may form a portion of the rotor assembly 94 and is rotatably held within the head 86. The bearing member 98 is symmetrical about a rotation axis 100 of the rotor assembly 94. A mating bearing member 102 may be attached distally with respect to the drive shaft distal end 90 such that the bearing member 98 matingly couples with the mating bearing member 102 (a concave surface shown below that mates with the curved convex surface of bearing member 98) as the drive shaft 88 and the rotor assembly 94 are rotated. The bearing member 98 contacts less than half of the mating bearing member 102 during rotation and is shown in more detail below. In the example shown, only the semi-spherical bearing member 98 contacts the mating bearing member 102 during rotation. The flat portion 104 and the tapered portion 106 are formed to not contact mating bearing member 102 during rotation. This ensures that the no opposing rotational forces are encountered between bearing member 98 and mating bearing member 102. If bearing member 98 contacted more than half of mating bearing member 102, the other half of mating bearing member 102 would be rotating in an opposite direction of bearing member 98 causing unwanted resistance to the desired rotation of rotor assembly. Such unwanted resistance may require a greater driving force from handpiece 10 and could create undesirable heat build-up in the gear assembly. In addition, structure may form a void 108 radially inward with respect to a plurality of teeth 110 forming the face-gear 92, as shown in FIG. 10. The void 108 provides space for the insertion of lubricant that is well-placed to lubricate the gears 92 and 96 to further assist in smooth, easy rotation of the rotor assembly 94.

The bearing member 98 of the disclosed example may include a convex bearing surface as shown and the mating bearing member 102 may include a mating concave bearing surface 112, shown in FIG. 10. Other mating bearing configurations may be used; for example, the bearing member could be formed from a flat, chamfered surface and mate with a corresponding flat, chamfered surface of the mating bearing member. The mating bearing member 102 may further include structure defining a central void 114 extending below the concave bearing surface 112. The central void 114 further reduces the contact surface between the bearing member 98 and the mating bearing member 102. In addition, the central void 114 has a benefit during manufacturing of providing a gate release location for injection molding the drive shaft 88, face-gear 92, and the mating bearing member 102 as a single unit. The central void 114 accommodates any material remnants from the gate release, thus reducing potential labor needed post-injection to knock-off remnant material and smooth the bearing surface 112. This assists in enabling the manufacture of reliable components at a reduced cost, compared to a bearing surface 112 formed without central void 114.

Figure 11:
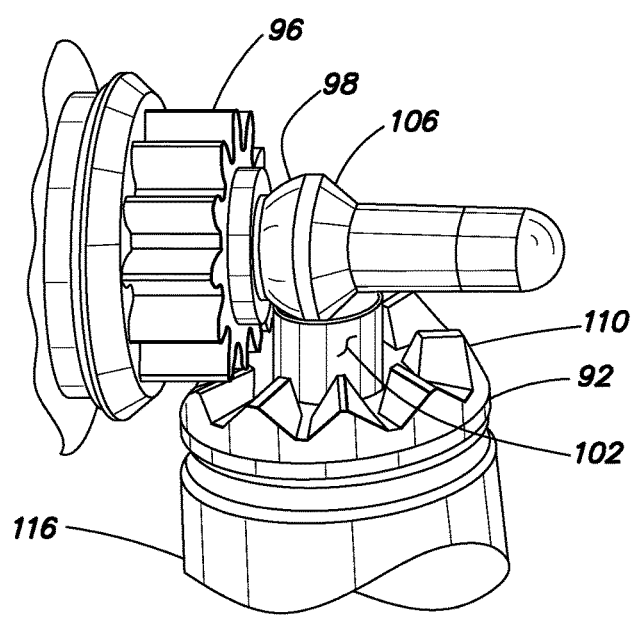
FIG. 11 is a partial perspective of a portion of the example prophy angle.

FIG. 11 shows the gear assembly of face-gear 92 and spur-gear 96 without head 86. This view illustrates the relationship between bearing member 98 and mating bearing member 102 where bearing member 98 contacts less than half of the mating bearing member 102 during rotation.

Figure 12:
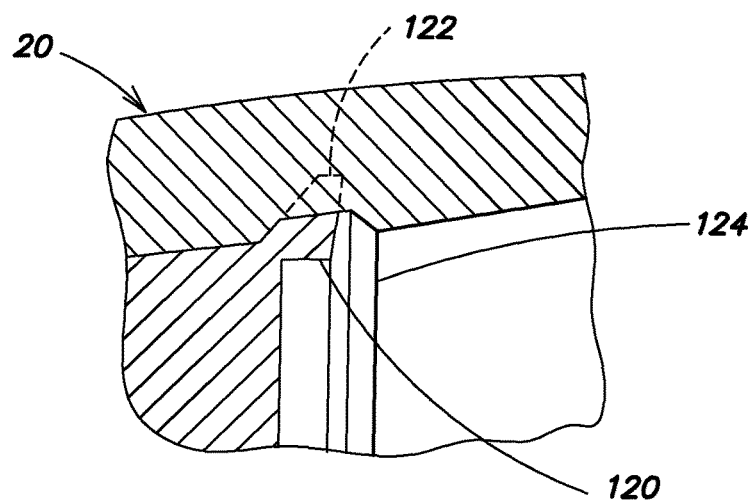
FIG. 12 is a partial perspective detailing a connection between to components of FIG. 9.

Referring back to FIG. 9, dental prophy angle 12 may include the proximal body 20 for attachment to a dental handpiece nosecone 16 and the drive shaft 88 rotatably held within the proximal body 20. The drive shaft 88 may also extend beyond a proximal end of the prophy angle 12. A retainer 116 (shown in cross section) may be held within the proximal body 20 surrounding a portion of the drive shaft 88. A distal end 118 of the retainer 116 may form a bearing surface for the gear 92 attached to the distal end 90 of the drive shaft 88. A retention boss 120 may be formed on and surrounding the retainer 116, wherein a cross-section of the retention boss tapers to an outer edge 122, as shown. A retention groove 124 may be formed in the proximal body 20 for mating attachment with the retention boss 120 such that a portion of the retention boss 120 is compressed within the retention groove 124. This is best shown in FIG. 12 that illustrates the connection between the retention boss 120 and the retention groove 124 in detail. The dashed line illustrates where outer edge 122 would lie in an uncompressed state compared to the compressed state shown. This compression of retention boss 120 within retention groove 124 provides a robust connection and ensures that drive shaft 88 aligns face-gear 92 and mating bearing member 102 properly with spur-gear 96 and bearing member 98 during use, as force is applied to the prophy angle 12 against a patient's teeth. An exterior of the retainer 116 may also include at least one raised annular rib 126 for frictional contact with the proximal body 20. The annular rib 126 is shown as a dashed line because it is optional. The raised annular rib 126 may provide additional frictional contact with the proximal body 20.

Figure 13:
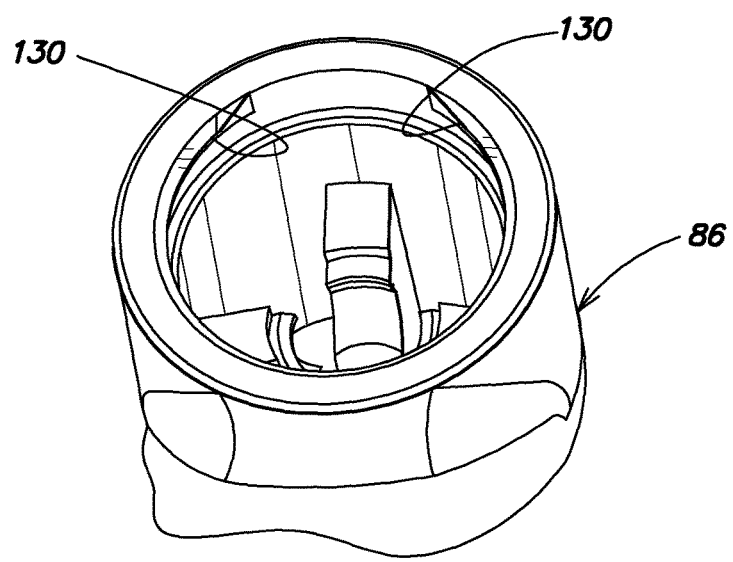
FIG. 13 is a partial perspective of a portion of the example prophy angle.

The dental prophy angle 12 may include the proximal body 20 for attachment to a dental handpiece nosecone 16, the head 86 may be formed on a distal end of the proximal body 20 and the rotor assembly 94, including the portion 95 rotatably held within the head 86. The rotor assembly may further include a retention flange 128 extending radially from the rotor assembly 94 as shown in FIG. 9. A corresponding retention boss 130 may extending from an interior surface of the head 86 and is located above the rotor assembly retention flange 128 when the rotor assembly 94 is mounted within head 86. The retention boss 130 may form an arc of less than three hundred sixty degrees. Forming the retention boss 130 at less than a full, complete, three hundred sixty degree ring allows room for an injection molding form to be pulled from head 86 without stressing and deforming the shape of the opening in head 86. The retention boss 130 is best seen in FIG. 13.

The prophy angle 12 and rotor assembly 94 may further include a button 132 with a plurality of radial protrusions 134. The button 132 and radial protrusions 134 are for frictional contact with a dental prophy cup. The button 132 and protrusions 134 are only one example and they may have any appropriate form factor for non-slip engagement with a prophy cup during use.

The dental prophy cup 136 may include a body 138 having a proximal portion 140 and a distal portion 142, as shown in FIGS. 14 and 15. A cup 144 may be formed on the body distal portion 142. A rotor cavity 146 may be formed within the body proximal portion 140. A rotor contact surface 148 forms a portion of the rotor cavity 146 including a profile for matingly coupling with a rotor surface (such as the button 132 and radial protrusions 134 shown in FIG. 9). The rotor contact surface 148 profile may include a plurality of radial recesses 150 for matingly coupling with the plurality of radial protrusions 134 formed on a top surface of the prophy angle rotor 94. Providing mating surfaces between the prophy cup 136 and the rotor assembly 94 including the mating radial recesses 150 and radial protrusions 134 positive, robust, non-slip contact is achieved, even as the rotor assembly is rotated at a high rate and force is applied against a patient's teeth.

The dental prophy cup 136 may further include a proximal end 152 of the body 138 forming a skirt 154 for surrounding a flange 156 (shown in FIG. 9) of the prophy angle rotor 94. The flange 156 is held externally with respect to the head 86 of the prophy angle 12 when the rotor assembly 94 is mounted within the head 86. The skirt 154 acts as a rotating seal to reduce the amount and likelihood of moisture and debris entering inside head 86 during use, thus helping to provide reliable, stable, smooth rotation of the prophy cup 136. FIG. 16 shows a partial perspective view of prophy angle 12 with prophy cup 136 mounted on the rotor assembly 94 (not seen) that is held within head 86. Prophy cup 136 may be formed of silicone or other appropriate pliable resilient material that will stretch to be placed over the button 132 and flange 156 and that will deform against a patient's teeth under pressure during use.

FIGS. 17A, 17B, and 17C are examples showing the benefits of providing handpieces 10 with an integer multiple of three number of finger recesses 52, 54. Such an integer multiple of three number provides a user with a comfortable, stable grip because a typical position of a user's fingers 158 gripping a handpiece 10 will be as shown in FIG. 17A. This position may be described as creating an equilateral triangle between the contact points of each finger 158 and the handpiece 10. The equilateral triangle is shown in FIG. 17B, where a user's fingers 158 are shown without handpiece 10 so that equilateral triangle 160 may be clearly shown. It is also noted that the hand grip of FIG. 17A is slightly different from the hand grip of FIG. 17B, yet the equilateral triangle is still formed. FIG. 17C shows an end view of an example handpiece 10, with finger recesses 52, 54, and with the equilateral triangle 160 showing a typical hand grip contact points. The example shown is with respect to finger recesses 52 but the same explanation applies to finger recesses 54. It was discovered that providing an integer multiple of three number of finger recesses spaced about the periphery of handpiece 10 provides a user with a comfortable, reliable, and consistent hand grip location.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A combination of a dental handpiece and a prophy angle comprising:
    the dental handpiece including a body and a nosecone threadably connected to a distal portion of the dental handpiece;
    the prophy angle including a proximal body such that the prophy angle proximal body is matingly attached to the nosecone;
    a plurality of elongated torque members formed on each of the prophy angle proximal body and the nosecone, wherein each of the plurality of elongated torque members is one of a male torque member and a female torque member, such that each male torque member formed on one of the prophy angle proximal body and the nosecone matingly couples with a female torque member formed on the other of the nosecone and the prophy angle proximal body; and
    wherein the prophy angle proximal body frictionally attaches to a known standard doriot-style nosecone and the dental handpiece nosecone is formed to prevent attachment to a known standard doriot-style prophy angle.

2. The combination of claim 1 wherein the distal portion of the dental handpiece includes a ball nose.

3. The combination of claim 1 wherein the proximal body is matingly coupled to the nosecone via a frictional interference.

4. The combination of claim 1 wherein the nosecone includes three male torque members and the prophy angle includes three female torque members.

5. A dental handpiece comprising:
    a body;
    a nosecone threadably connected to a distal portion of the dental handpiece;
    a plurality of elongated torque members formed on the nosecone, wherein each of the plurality of elongated torque members is one of a male torque member and a female torque member, such that each male torque member formed on the nosecone is for matingly coupling with a female torque member formed on a mating prophy angle proximal body; and
    wherein the nosecone, including the plurality of elongated torque members formed on nosecone, is formed to prevent attachment to a known standard doriot-style prophy angle.

6. The dental handpiece of claim 5 wherein the distal portion of the dental handpiece includes a ball nose.

7. The dental handpiece of claim 5 wherein the mating coupling between the nosecone and the mating prophy angle proximal body is via a frictional interference.

8. The dental handpiece of claim 5 wherein the nosecone includes three male torque members.

9. The dental handpiece of claim 8 wherein a circumference defined by a top surface of each of the three male torque members is sufficiently large to prevent the attachment of the nosecone to the known standard doriot-style prophy angle.

10. The dental handpiece of claim 5 wherein a circumference of an outermost top surface of the nosecone is sufficiently large to prevent the attachment of the nosecone to the known standard doriot-style prophy angle.

11. A prophy angle comprising:
a proximal body;
a plurality of elongated torque members formed on the prophy angle proximal body, wherein each of the plurality of torque members is one of a male torque member and a female torque member, such that each male torque member formed on the prophy angle proximal body is for matingly coupling with a female torque member formed on a mating dental handpiece nosecone; and
wherein the prophy angle proximal body frictionally attaches to a known standard doriot-style dental handpiece nosecone.

12. The prophy angle of claim 11 wherein the proximal body is matingly coupled to the mating dental handpiece nosecone via a frictional interference.

13. The prophy angle of claim 11 wherein the proximal body includes three female torque members.

14. The combination of claim 13 wherein a portion of the proximal body, not including structure forming the three female torque members, frictionally attaches to the known standard doriot-style nosecone.

15. A dental handpiece comprising:
a body; and
a nosecone assembly attached to a distal portion of the body, the nosecone assembly including:
a proximal base section for attachment to the handpiece body distal portion;
a ball nose pivotally engaged with the proximal base section;
a ball lock surrounding a portion of the proximal base section and a portion of the ball nose;
a flexible ring seal surrounding a portion of the ball nose, wherein the flexible ring seal is positioned between the ball nose and an interior surface of the ball lock;
a nosecone threadably coupled with the ball nose;
a locking seal for surrounding a distal end of the ball lock and the proximal base section of the nosecone; and
wherein, as the nosecone is increasingly threaded onto the ball nose, a frictional contact force is increased between the ball lock and each of the proximal base section, the ball nose, and the locking seal.

16. The dental handpiece of claim 15 further including an engine cartridge held within the body, wherein the engine cartridge is sized and adapted for containing one of a plurality of engine types;
the engine cartridge further including a drive member extending from an engine cartridge distal end, the drive member being rotatably driven by one of the plurality of engine types and the engine cartridge including a proximal end for connection to one of a plurality of types of power source connectors; and
wherein a proximal end of the body includes structure for connection to each of the plurality of types of power source connectors.

17. The dental handpiece of claim 15 wherein the proximal base section is formed of aluminum.

18. The dental handpiece of claim 15 wherein the ball nose is formed of aluminum including at least a partially anodized exterior surface.

19. The dental handpiece of claim 15 wherein the ball lock is formed of aluminum including at least a partially anodized exterior surface.

20. The dental handpiece of claim 15 wherein the nosecone is formed of aluminum including at least a partially anodized exterior surface.

21. The dental handpiece of claim 15 wherein the locking seal is formed of plastic and has a portion of an interior surface roughened.

22. The dental handpiece of claim 15 wherein at least a frictional contact surface of each of the ball nose, the ball lock, and the locking seal is roughened for enhancing the frictional contact force.

23. The dental handpiece of claim 15 further including a plurality of finger recesses equally spaced and formed around a periphery of each of the ball lock and the locking seal wherein a number of finger recesses is an integer multiple of three.

* * * * *